United States Patent [19]
Chou et al.

[11] Patent Number: 5,452,391
[45] Date of Patent: Sep. 19, 1995

[54] REUSABLE OPTICAL FIBER CONNECTOR ADAPTER WITH OPTICAL BARRIER

[75] Inventors: Marilyn M. Chou, Oakland; Kwok H. Ngai, San Francisco; King J. J. Yu; Ken T. Yu, both of Oakland, all of Calif.

[73] Assignee: Xintec Corporation, Oakland, Calif.

[21] Appl. No.: 264,079

[22] Filed: Jun. 22, 1994

[51] Int. Cl.⁶ .............................................. G02B 6/42
[52] U.S. Cl. ................................... 385/92; 385/53; 385/78; 385/902
[58] Field of Search ................. 385/31, 38, 53, 60, 385/76–78, 86–88, 92, 117–119, 123, 125, 147, 902

[56] References Cited

U.S. PATENT DOCUMENTS

| | | | |
|---|---|---|---|
| 4,273,109 | 6/1981 | Enderby | 385/77 X |
| 4,583,539 | 4/1986 | Karlin et al. | 385/125 X |
| 4,707,073 | 11/1987 | Kocher | 385/902 X |
| 4,722,337 | 2/1988 | Losch et al. | 128/303.1 |
| 4,785,805 | 11/1988 | Joffe et al. | 128/303.1 |
| 4,895,145 | 1/1990 | Joffe et al. | 606/11 |
| 5,085,492 | 2/1992 | Kelsoe et al. | 385/60 |
| 5,104,242 | 4/1992 | Ishikawa | 385/53 |
| 5,136,676 | 8/1992 | Arnett et al. | 385/119 |
| 5,348,487 | 9/1994 | Marazzi et al. | 385/78 X |
| 5,363,460 | 11/1994 | Marazzi et al. | 385/77 X |

*Primary Examiner*—John D. Lee
*Attorney, Agent, or Firm*—Ray K. Shahani; James J. Leary

[57] ABSTRACT

A reusable connector adapter for coupling a fiber optic laser delivery device with a laser source having a laser energy output port. The adapter allows the use of a variety of different laser sources with a variety of different fiber optic laser delivery devices. The adapter maintains the fiber optic laser delivery device adjacent to the laser energy output port such that the laser energy to be transmitted is communicated efficiently to the fiber optic laser delivery device. The adapter further comprises a laser interlock deactivation means such that if a laser source has a mechanical, electrical or optical interlock system, the adapter will function to deactivate the interlock system. Furthermore, the adapter also comprises an optical barrier to prevent the unintended transmission of laser energy when, for example, the fiber optic laser delivery device has not been installed or has not been installed properly.

33 Claims, 4 Drawing Sheets

REUSABLE OPTICAL FIBER CONNECTOR ADAPTER WITH OPTICAL BARRIER

FIELD OF THE INVENTION

This invention relates generally to laser delivery systems and related accessories, and more particularly to a device which will allow the use of a variety of optical fiber medical laser scalpels or other optical laser transmission devices manufactured with various connection means in conjunction with a variety of laser generating sources.

BACKGROUND OF THE INVENTION

Although the first useful lasers were developed in the 1960's, recent advances in laser and fiber optic delivery systems have greatly enhanced the use of this technology in the field of medicine and other fields. Today there is a wide variety of laser delivery systems available on the market intended for use in a wide range of applications.

A common type of laser known as a $CO_2$ laser delivers radiation with a wavelength of 10.64 microns. However, in order to focus or channel the radiated energy produced by a $CO_2$ laser it is necessary to configure sets of mirrors in certain ways. These systems are typically large and expensive. With the advent of the Nd:YAG type laser delivering electromagnetic energy at a wavelength of 1.064 microns, it became possible to generate and focus the laser radiation through a silica core optical fiber. Thus, fiber optic surgical tools have become important in certain procedures. The range of their utility is still being explored and discovered.

Laser fibers are used in different ways, including incision, necrosis or killing of live tissue, excision or removal of tissue and structure, and cauterization of tissue. A very focused beam would provide the greatest amount of control during either operation. Cauterization and necrosis of living tissue is accomplished by coagulation, or more precisely with respect to the laser itself, by photocoagulation of contacted or penetrated tissue. In this process the laser beam causes the proteins in the contacted tissue to heat up rapidly and thermally denature. This essentially kills living tissue and seals blood vessels. In practice, during an incision procedure cauterization of the incised tissue is likely to occur simultaneously. Thus, laser surgery is often characterized by an absence of bleeding during the surgery.

Given the recent advances in related surgical and other laser technology, it has become increasingly important to provide users of such equipment with a range of specific tools, accessories and laser generating systems. Many manufacturers are engaged in these activities. A range of laser drivers or laser generators are now in use in hospitals and clinics throughout the world. These laser systems are expensive and constitute capital investments. Additionally, there is a very broad range of accessories to be used with these laser systems. Unfortunately, compatibility between the accessories of one manufacturer, though perhaps optimally suited for the particular application or need of the surgeon, and the laser system available to the surgeon is not always possible.

On a laser generating system there is always an output interface between the device generating the laser energy and the device transmitting the laser energy. This interface must provide several functions. First, the interface must be convenient to use. Bayonet mounted, screw-in or other quick-connect means are often provided on the laser generators. Similarly, most fiber optic scalpels, probes and other devices incorporate a factory preassembled fiber connector to be used with a specific type of laser generator. In the industry, there are several types of fiber connectors which have become standard and are used widely, due either to market share of certain manufacturers as well as industry standards which have been developed in the last decade or two. One such standard connector is known as the SMA 905 connector. The fiber optic waveguide is connected to a metal tip which aligns and directs the beam into the fiber. This metal tip is affixed to the optical fiber. A bayonet type connector has a spring loaded mounting system (or some sort of keyed, insert and turn to lock) so that the tip can be brought into close contact or adjacent position with the output port of a laser source. Thus, as the spring is elongated and the bayonet mounting is employed, the fiber connector will ensure an efficient and safe communication of laser energy into the proximal end of the optical fiber. Other types of connectors, such as the EZ connector and others, generally have some sort of system whereby the proximal end of the fiber is positioned precisely and the fiber connector itself maintains the integrity of the interface between the laser source and the optical fiber instrument. It is important to note that the present invention includes the embodiment wherein a bare fiber is inserted into the multi-use connector adapter.

The interface assembly must provide an accurate and precise connection and transmission of the laser energy. Typically, a laser driver will employ a series of lenses or other focusing apparatuses such that the output of the laser can be directed entirely or as nearly entirely as possible into the receiving end of the optical fiber accessory. Many of the connectors available today as standard equipment on laser drivers as well as associated accessories transmit significantly less than 100% of the energy available at the interface. This is due to poor design and inefficient coupling of the optical fiber assembly to the laser source.

Finally, all laser delivery systems require critical safety protocol to safeguard against injury during operation. Often laser generating systems are equipped with ambient or stray beam sensors. Thus, for, example, if the surgical instrument being used to deliver the laser energy to the point of surgical operation is dropped or inadvertently directed to a point other than where it is intended to be used, the laser source shuts off. A stray laser beam can cause serious injury to operating room personnel or equipment or to the patient or doctor themselves. For example, an instantaneous flash of laser energy at 1.064 microns delivered at a rate between 20 and 100 watts, typical usage rates, can cause permanent blinding or other bodily damage.

Another safety feature of various laser generating systems comprises an interface assembly interlock system. This type of system insures that the laser cannot be operated unless properly connected to a delivery system. The interlock can be mechanical, electro-mechanical or electrical. In one system, an "electronic signature" is used. In this arrangement, at the laser output interface with the delivery apparatus, a distinctive electrical signal is produced by the coupling of the apparatus and the laser generator such that absent said distinctive electrical signature, the laser generator will not operate. This ensures that a proper connection is made between the laser and the delivery system and will prevent the transmission of laser energy unless and until the transmission is intended. Otherwise, stray laser beams can cause serious bodily and property damage.

The principle problem with all of the laser systems described above is that each manufacturer's equipment utilizes a slightly different connector and interface system. However, if a certain medical facility has invested in a laser generating system, the delivery system or other accessory options available to that facility are limited by the range of products manufactured by the same manufacturer of the laser generating system. There is a high degree on incompatibility among product designs and often certain laser equipment is unavailable to a medical practitioner due to the variations in laser connector designs. Although many of the accessories available today have become industry standards and commonplace among users, there is still a wide range of accessories which are manufactured by different manufacturers according to individual manufacturer's specific criteria and specifications.

U.S. Pat. No. 4,722,337 (Losch et al) discloses a medical laser peripheral and connector system having essentially two portions, a connector plug portion and a fiber portion. Both portions are fused together. Thus, after use of the delivery system, the entire assembly must be discarded since the optical fiber portion cannot be reused.

U.S. Pat No. 4,785,805 (Joffe et al) discloses a two piece disposable laser delivery system which is also comprised of two separable portions. One portion, the head, is reusable while the other portion, though not reusable, is disposable and can be replaced. However, the reusable portion is designed to be used only with a specific type of disposable portion and is, therefore, not suitable for use with other disposable fiber optic delivery systems.

It is therefore an object of this invention to overcome the above cited problems with the existing technology, namely inherent design non-compatibility between various types of commercially available laser equipment, including laser generators and delivery systems.

SUMMARY OF THE INVENTION

This invention is designed to bridge the gap between industry standard laser peripherals and accessories and those manufactured to less common specifications. This invention will allow owners and users of different types of fiber optic or other laser delivery devices and laser sources to use non-standard or other peculiarly designed accessories and laser sources interchangeably.

A reusable connector adapter for coupling a laser source to a fiber optic laser delivery device is disclosed herein. The laser source would have an output port and the fiber optic laser delivery device would have a laser receiving end with a fiber connector at the laser receiving end. Additionally, the fiber optic laser delivery device has a fiber optic waveguide. The reusable connector adapter consists of a connector plug portion with a proximal end which is precisely shaped so as to couple efficiently with the laser source. The proximal end of the connector plug portion has a laser source attachment means such that the connector plug portion can be attached securely to and maintained adjacent to the output port of the laser source in an operative position. The attachment means can be any connector means or attachment device or method or design so as to maintain the integrity of the optical communication between the laser source and the fiber optic laser delivery device. This means would include matching threaded portions, twist locking or bayonet mounting fittings and other means known to those skilled in the art. The connector plug portion also has a distal end and a central hollow body portion intermediate the proximal end and the distal end for receiving and containing the fiber connector within the central hollow body portion, in efficient optical communication with the laser source. The reusable adapter connector also consists of a fiber optic laser delivery device securing portion for removably maintaining and securing the fiber optic laser delivery device within the central hollow body portion of the connector plug portion.

The invention further consists, as part of the connector plug portion of the reusable connector adapter, a laser interlock deactivation means for use with a laser source that has a laser interlock for preventing the undesired transmission of laser energy unless and until such time as the interlock is deactivated. When the laser interlock comprises a mechanical switch, the laser interlock deactivation means can engage the mechanical switch such that the laser source interlock is deactivated. Similarly, when the laser interlock requires an electrical signature generated by an electrical signature generating circuit for deactivation of the laser interlock, or when the laser interlock requires a certain optical signal, the laser interlock deactivation means of the reusable connector adapter further comprises a portion or all of an electrical signature generating circuit or an optical signal generating signal.

The reusable connector adapter further comprises an optical barrier for preventing laser energy from being transmitted unless a fiber optic laser delivery device is properly installed within the reusable connector adapter. The optical barrier can be made of an optically opaque material. However, depending upon the application, the barrier can absorb or reflect or a combination of both, and the precise design, construct or materials of construction can be modified as desired. Optionally, the optical barrier is mounted within the central hollow body portion of the connector plug portion such that upon insertion of the fiber optic laser delivery device into the reusable connector adapter, the optical barrier is removed from the path of transmission of laser energy. In some embodiments the optical barrier is adjacent the proximal end of the connector plug portion. In other embodiments, the optical barrier is adjacent the fiber optic laser delivery device securing portion of the reusable connector adapter. Optionally, the optical barrier is pivotally mounted on a spring member. Optionally, the optical barrier is mounted within the central hollow body portion of the connector plug portion adjacent to the distal end of the connector plug portion.

When the interlock system requires a mechanical or electrical contact between the proximal end of the connector plug portion and the output port of the laser source for deactivation of the laser interlock, a laser interlock deactivation means which comprises a contacting element, is included in the reusable connector adapter. In some embodiments the contacting element is retractable. In some embodiments, the retractable contacting element is in a retracted position in the absence of the fiber optic laser delivery device and in an extended position when the fiber connector of the fiber optic laser delivery device is received within the connector plug portion, such that when the retractable element is extended, the contacting element is in electrical or mechanical contact with the output port of the laser source.

The fiber optic laser delivery device securing portion comprises an engagement means for coupling the fiber optic laser delivery device fiber securing portion to the connector plug portion, thereby maintaining the fiber optic laser delivery device within the central hollow body portion. This engagement means would be any useful, efficient coupling system, such as a bayonet mounting, matching threaded portions, or other snap-on or compression fitting, and would be apparent to those skilled in the art. In one embodiment, the engagement means comprises a biasing element for maintaining the fiber optic laser delivery device within the central hollow body portion biased between the connector plug portion and the fiber optic laser delivery device securing portion. This could be a spring member.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE INVENTION

Figure 2:
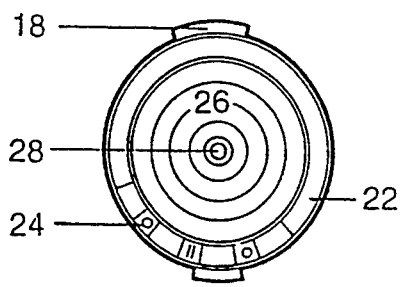
FIG. 2 is a front view of an embodiment of the apparatus of the present invention.
Figure 1:
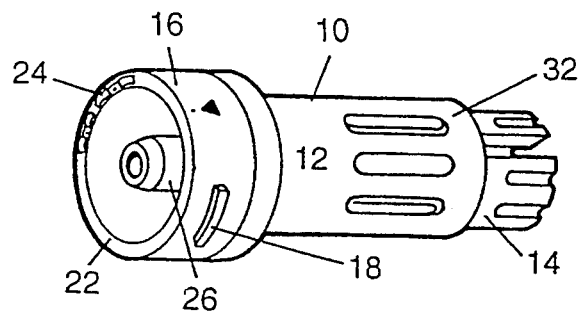
FIG. 1 is a perspective view of an embodiment of the apparatus of the present invention.
Figure 3:
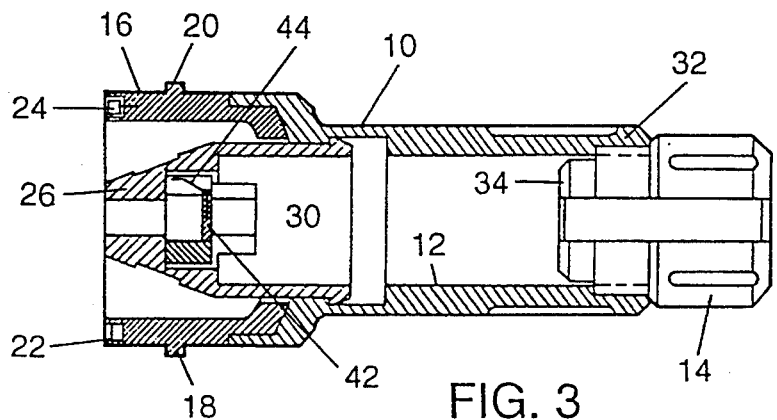
FIG. 3 is a side cross section view of an embodiment of the apparatus of the present invention.
Figure 4:
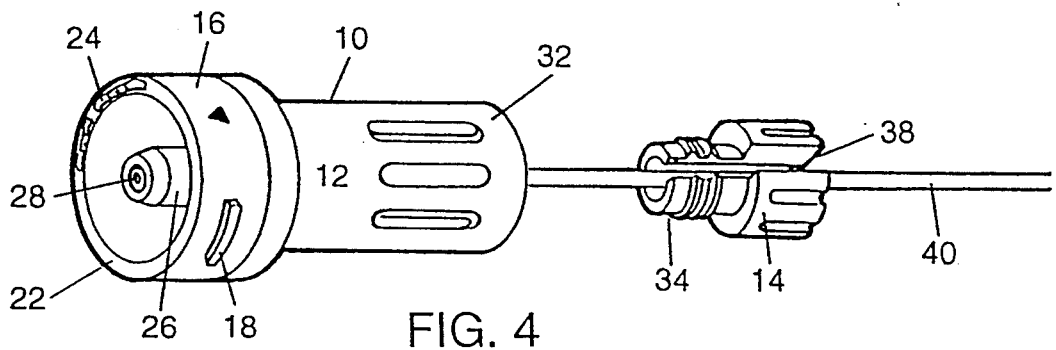
FIG. 4 is a perspective view of an embodiment of the apparatus of the present invention with a fiber optic laser delivery device installed therein.

With respect to FIGS. 1–5, the reusable connector adapter 10 is essentially comprised of two portions, the connector plug portion 12 and the fiber securing portion 14. The proximal end 16 of the connector plug portion is formed such that it is received by the output port of a laser source (not shown). Opposing tabs 18 and 20 form a bayonet-type mounting for connecting the connector plug portion of the reusable connector adapter to the output port of the laser source. Any of a variety of laser source attachment means may be selected, depending upon the precise application and configuration of other equipment in use, including threads, clamps, compression fitting, or other laser source attachment means known to those skilled in the art. A circumferential groove 22 in the proximal end of the connector plug portion of the reusable connector adapter contains a plurality of metal contacts 24 secured therein. The presence of the metal contacts is only required if the laser source is equipped with a laser interlock system whereby the control electronics or some mechanical device or control program of the laser source prevents the transmission of laser energy unless an electronic circuit is closed. These metal contacts, therefore, serve to provide a signature signal, its precise format or type of signal depending upon the requirements of the laser source interlock, to the control electronics of the laser source. Unless and until the metal contacts close the required circuit or supply the required electronic signature, the laser interlock system prevents the transmission of laser energy. This control circuit may also serve to identify to the laser source the type of laser peripheral being employed. When the laser interlock comprises a mechanical switch, the laser interlock deactivation means can engage the mechanical switch such that the laser source interlock is deactivated. Similarly, when the laser interlock requires an electrical signature generated by an electrical signature generating circuit for deactivation of the laser interlock, or when the laser interlock requires a certain optical signal, the laser interlock deactivation means of the reusable connector adapter further comprises a portior or all of an electrical signature generating circuit or an optical signal generating signal.

Figure 5:
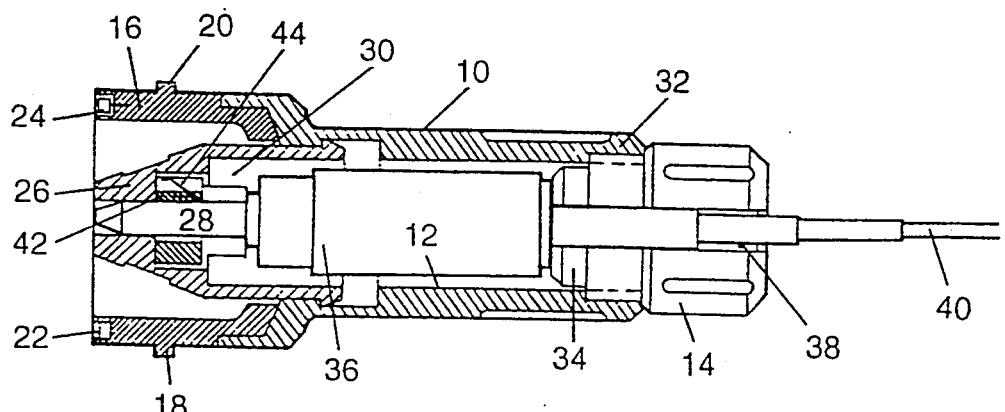
FIG. 5 is a side cross section view of an embodiment of the apparatus of the present invention with a fiber optic laser delivery device installed therein.
Figure 7:
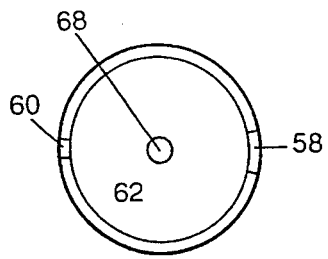
FIG. 7 is a side cross section view of an embodiment of the apparatus of the present invention.
Figure 6:
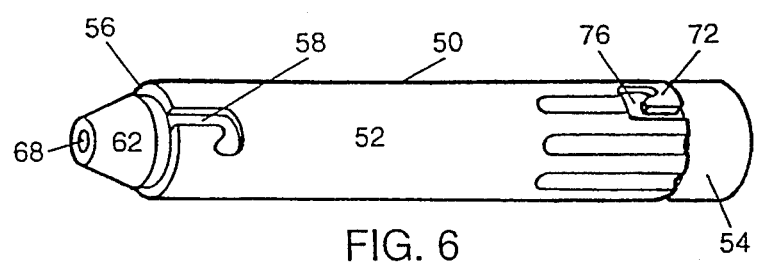
FIG. 6 is a perspective view of an embodiment of the apparatus of the present invention.
Figure 8:
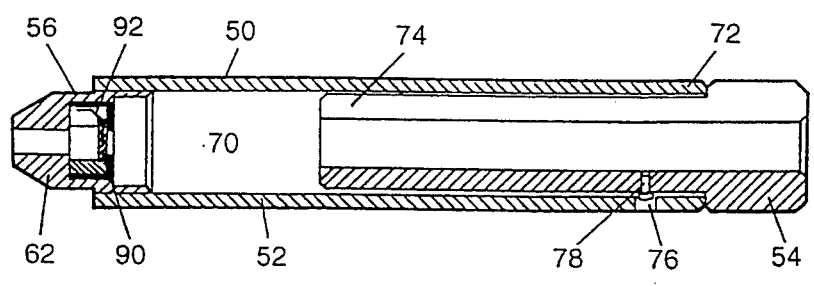
FIG. 8 is a perspective view of an embodiment of the apparatus of the present invention with a fiber optic laser delivery device installed therein.
Figure 9:
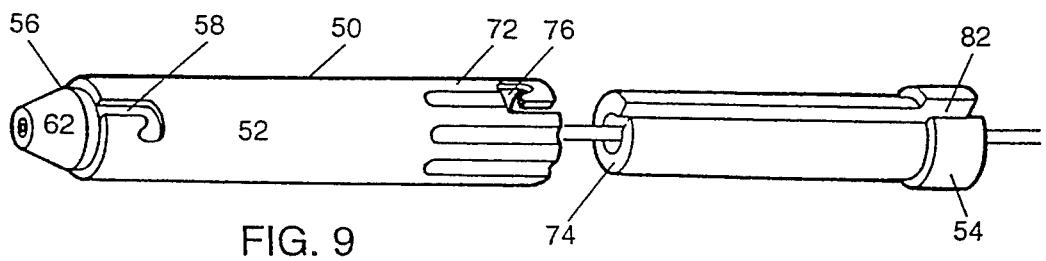
FIG. 9 is a side cross section view of an embodiment of the apparatus of the present invention with a fiber optic laser delivery device installed therein.

A generally conical shaped central member 26 is formed so as to receive the proximal end 28 of a fiber optic laser delivery device from the inside annular region 30 of the proximal end of the connector plug portion. This conical shaped central member forms a physical matching connection between the laser source and the fiber optic laser delivery device by positioning the proximal end of the fiber optic laser delivery device accurately and precisely adjacent to the output port of the laser source, thereby allowing laser energy to be communicated directly and efficiently from the laser source into the proximal end of the fiber optic laser delivery device. This highly efficient optical communication between the laser source and the fiber optic laser delivery device is very important to protect the integrity of the connector adapter and the laser source output port. The distal end 32 of the connector plug portion can be engaged by the proximal end 34 of the fiber securing portion of the present invention. This engagement can be accomplished by providing matching, threaded portions or other adjustable and detachable or loosening connecting means. Therefore, as best shown by FIG. 5, the fiber optic laser delivery device is held securely in place by being inserted into the connector plug portion of the reusable connector and having the fiber securing portion installed. The fiber connector 36 is maintained in place by being inserted between the conical shaped central member, at the proximal end of the reusable connector adapter, and by the proximal end of the fiber securing portion. It is important to note that this fiber connector can be a standard SMA 905, EZ or other standard or non-standard fiber connector. A slot 38 is provided in the fiber securing portion so as to allow the portion to be slipped over the fiber optic portion of the laser delivery device and assembled efficiently and conveniently. Thus, the fiber optic portion 38 of the fiber optic laser delivery system is shown to extend from the distal end of the fiber securing portion of the reusable connector adapter.

As a safety feature of the invention, an optical barrier 42 is installed in the conical shaped central member. This optical barrier is held in a normally closed position by spring 44. Thus, in the event the reusable connector adapter is connected to a laser source and the laser source interlock system is deactivated and laser transmission is initiated without first inserting a fiber optic laser delivery device, then there will be no opportunity for the laser source to be released into the surrounding operating room or other environment. This is very important in operation. As is well known, a stray laser beam in a medical operating room or in most any other application would have the potential to cause serious damage to surgeons, technicians, patients, observers, or any equipment in the vicinity.

The material of construction of the optical barrier is very important. For one embodiment, any material which does not absorb electromagnetic energy in the infrared frequencies would be adequate so that the optical barrier doesn't get too hot or become destroyed due to incident laser energy. However, depending upon the application, the barrier can absorb or reflect or a combination of both, and the precise design, construct or materials of construction can be modified as desired. Absorption of energy could be a valuable function if overheating becomes a problem. Materials such as aluminum, stainless steel, plastics or other metals or polymeric materials might be used, optionally with a coating or barrier to prevent absorption by the infrared laser energy, and the precise composition of the material of construction of the optical barrier would be determined depending upon the application. Furthermore, the precise location of the optical barrier can be determined based upon the individual application or instrument design. For example, in certain embodiments it may be advantageous to have the optical barrier placed close to the receiving end of the connector adapter of the present invention so as to prevent transmission beyond the connector adapter by as much as possible. Alternatively, it may be important to dispose the optical barrier towards the back part of the connector on the back part of the connector. In this manner, if laser energy is directed onto the optical barrier and any damage results, any damage to the laser source itself will be minimized by displacing the optical barrier as far back on the connector as possible.

FIGS. 6–10 show various views of another embodiment of the apparatus of the present invention. In this embodiment, the reusable connector adapter 50 is essentially comprised of two portions, the connector plug portion 52 and the fiber securing portion 54. The proximal end 56 of the connector plug portion is formed such that it is received by the output port of a laser source (not shown). Opposing keys 58 and 60 (as illustrated most clearly by FIG. 7) form a keyed mounting system for connecting the connector plug portion of the reusable connector adapter to the output port of the laser source. In certain laser systems, the shape of the key at this location may serve a dual purpose: firstly, the key may serve to attach the reusable connector adapter to a laser source, and therefore is important to maintain integrity of the optical path. Secondly, some laser systems may require a certain shaped key at this position or some owher position on the reusable connector adapter itself, regardless of the mounting system employed between the reusable connector adaqter and the laser source, to provide a deactivation means for a laser interlock system. Thus, as the reusable connector adapter is installed onto the laser source, the laser interlock is turned off and laser transmission is made possible upon control by an operator.

Figure 10:
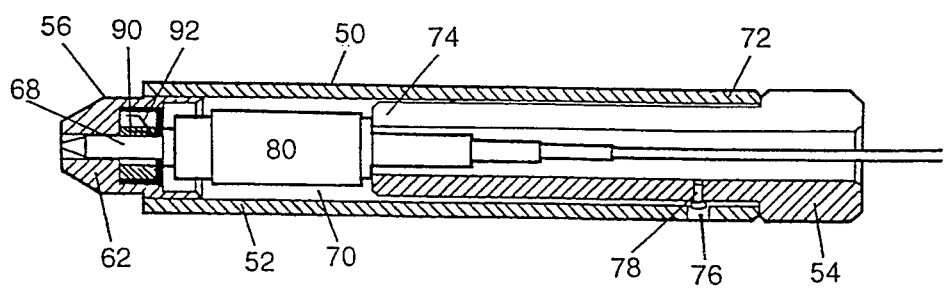
FIG. 10 is a perspective view of an embodiment of the apparatus of the present invention.
Figure 11:
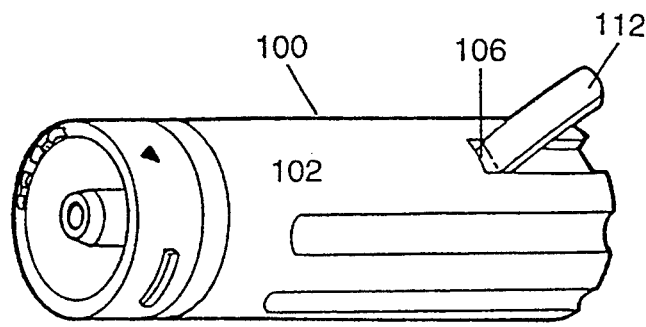
FIG. 11 is a front view of an embodiment of the apparatus of the present invention.
Figure 12:
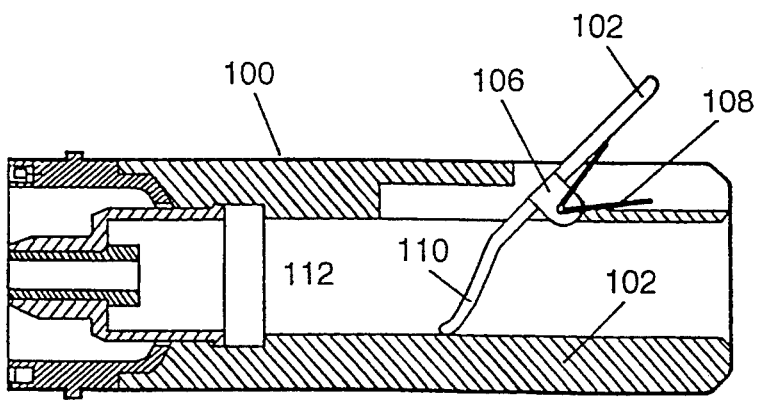
FIG. 12 is a side cross section view of an embodiment of the apparatus of the present invention.
Figure 13:
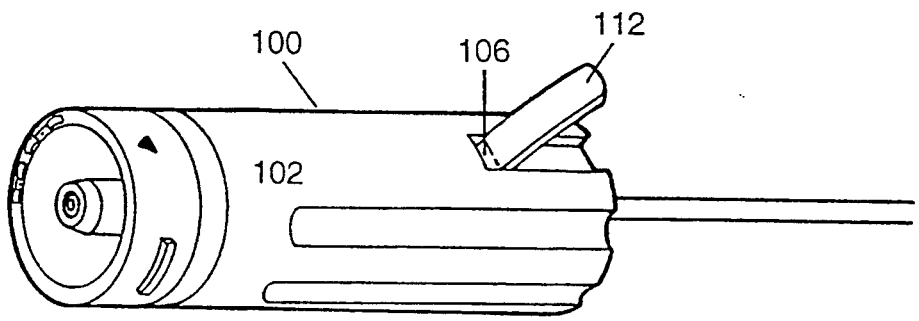
FIG. 13 is a perspective view of an embodiment of the apparatus of the present invention with a fiber optic laser delivery device installed therein.
Figure 14:
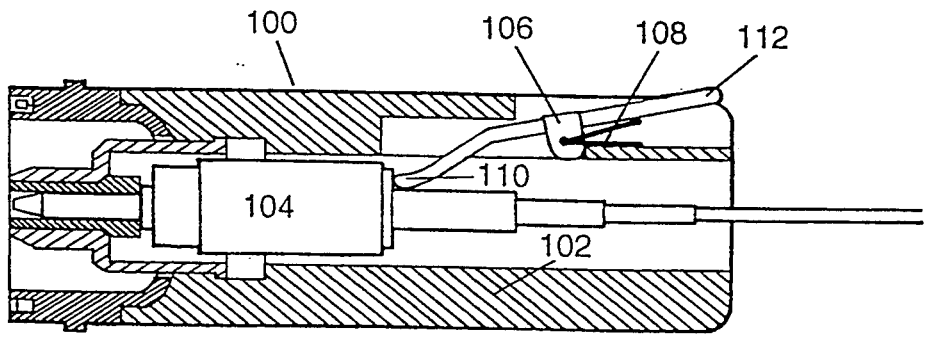
FIG. 14 is a side cross section view of an embodiment of the apparatus of the present invention with a fiber optic laser delivery device installed therein.

A generally conical shaped central member 62 is formed so as to receive the proximal end 68 of a fiber optic laser delivery device from the inside annular region 70 of the proximal end of the connector plug portion. This conical shaped central member forms a physical matching connection between the laser source and the fiber optic laser delivery device by positioning the proximal end of the fiber optic laser delivery device accurately and precisely adjacent to the output port of the laser source, thereby allowing laser energy to be communicated directly and efficiently from the laser source into the proximal end of the fiber optic laser delivery device. The distal end 72 of the connector plug portion can be engaged by the proximal end 74 of the fiber securing portion of the present invention. This engagement can be accomplished by providing matching, keyed portions or other detachable connecting means, shown here as a keyed groove 76 in the connector plug portion and a small axially extending stud 78. Therefore, as best shown by FIG. 10, the fiber optic laser delivery device is held securely in place by being inserted into the connector plug portion of the multi-use connector and having the fiber securing portion installed. The fiber connector 80 is maintained in place by being inserted between the conical shaped central member, at the proximal end of the reusable connector adapter, and by the proximal end of the fiber securing portion. A slot 82 is provided in the fiber securing portion so as to allow the portion to be slipped over the fiber optic portion of the laser delivery device and assembled efficiently and conveniently. Thus, the fiber optic portion 84 of the fiber optic laser delivery system is shown to extend from the distal end of the fiber securing portion of the reusable connector adapter.

As a safety feature of the invention, an optical barrier 90 is installed in the conical shaped central member. This optical barrier is held in a normally closed position by spring 92. Thus, in the event the reusable connector adapter is connected to a laser source and the laser source interlock system is deactivated and laser transmission is initiated without first inserting a fiber optic laser delivery device, then there will be no opportunity for the laser source to be released into the surrounding operating room or other environment. This is very important in operation. As is well known, a stray laser beam in a medical operating room or in any other application would have the potential to cause serious damage to surgeons, technicians, patients, observers, or any equipment in the vicinity.

FIGS. 11-14 show various views of another embodiment of an apparatus of the present invention. In this embodiment, the reusable connector adapter 100 consists essentially of a single plug connector portion 102. The embodiment shown is similar to that shown in FIGS. 1-5 and similar elements include opposing tabs for a bayonet mounting on the laser source, conical shaped central member for coupling the laser beam with the fiber optic laser delivery device, the metal contacts in the circumferential groove in the proximal end of the connector plug portion which serve to provide a signature signal or simply close a circuit required to deactivate the laser interlock, if any. Other similarities will be apparent.

In this embodiment, however, rather than providing a separate fiber securing or retaining portion, the fiber connector 104 is maintained in place, inserted securely between the proximal end of the connector plug portion and the optical barrier 106. Thus, it will be apparent that in this embodiment, the optical barrier serves a dual function: first, to prevent the unintended transmission of laser energy, and second, as a biasing element to bias the fiber connector toward the proximal tip of the reusable connector adapter so as to ensure integrity of the optical path. Spring 108 maintains the optical barrier in a normally closed position. As the fiber optic laser delivery device is inserted into the reusable connector adapter, the blocking portion 110 of the optical barrier is pivoted away from the open, annular region 112 of the reusable connector adapter. The tip of the blocking portion thus engages the fiber connector at a point 114, bearing upon the fiber connector and biasing the fiber connector toward the proximal end of the reusable connector adapter. In fiber optic laser delivery devices consisting of an SMA connector or some other fiber connector with a spring loaded fitting, the spring of the fiber connector maintains the biasing forces within the multi-use connector adapter so as to prevent movement of the fiber connector such that the optical path integrity is compromised, i.e. the optical path allows energy leakage, misalignment of the fiber and laser source output port occurs, etc.

To release the fiber device from the reusable connector adapter, the handle portion 112 of the optical barrier is manually depressed, thereby causing the blocking portion to be pivoted away from the fiber connector and optical fiber device. As best understood by FIG. 14, as the handle portion is depressed, the blocking portion would be moved into space 114, thereby allowing the fiber connector to be withdrawn. As will be understood, this embodiment provides a reusable connector adapter with essentially one part. Operation, i.e. installation and removal of a fiber optic laser delivery device, is greatly simplified.

FIGS. 15-18 show various views of another embodiment of the apparatus of the present invention. In this embodiment, the reusable connector adapter 120 is essentially comprised of two portions, the connector plug portion 122 and the fiber securing portion 124. The proximal end 126 of the connector plug portion is formed such that it is received by the output port of a laser source (not shown). Key 58 forms a keyed mounting system for connecting the connector plug portion of the reusable connector adapter to the output port of the laser source and is important to maintain integrity of the optical path.

Figure 15:
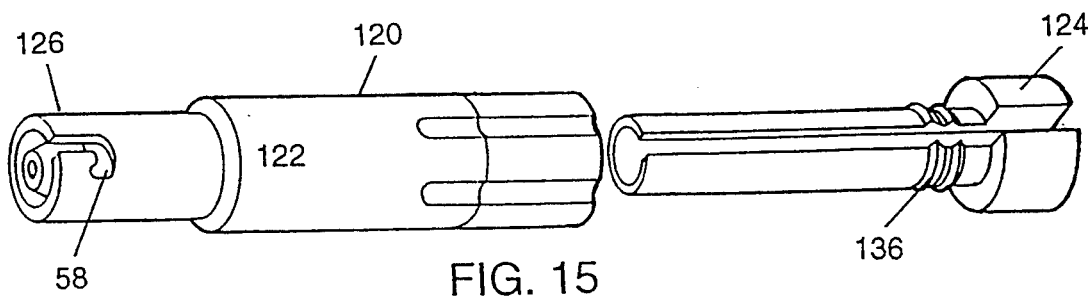
FIG. 15 is a perspective view of an embodiment of the apparatus of the present invention.
Figure 16:
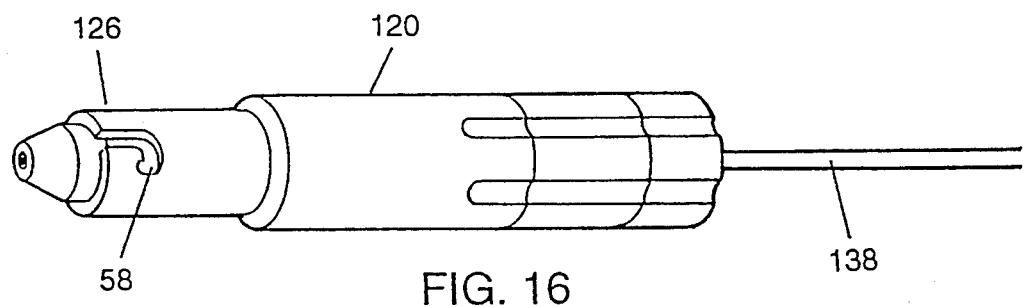
FIG. 16 is a perspective view of an embodiment of the apparatus of the present invention with a fiber optic laser delivery device installed therein.
Figure 17:
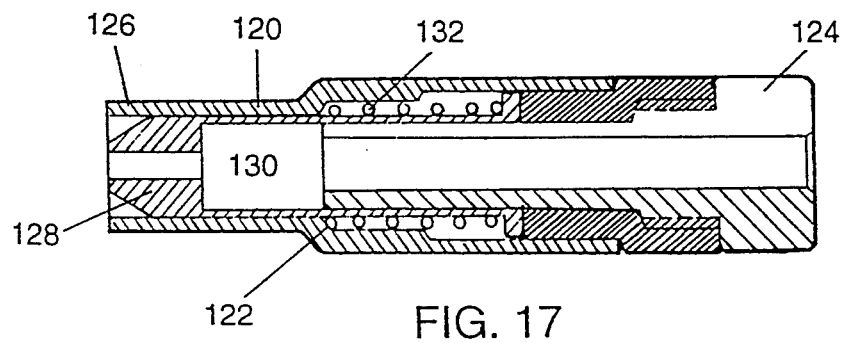
FIG. 17 is a side cross section view of an embodiment of the apparatus of the present invention.

In this embodiment, a retractable tip is provided at the proximal end of the connector plug portion. FIG. 15 shows the retractable tip retracted, as it would be without a fiber optic laser delivery device installed therein. FIG. 16 shows the assembly after the fiber has been installed in the adapter, with the tip extended. The purpose of this feature is to prevent the adapter from deactivating a laser interlock unless the system is ready. As mentioned previously, if the adapter were installed into a laser source output port and by the presence of the adapter the laser interlock were deactivated, injury could occur either to equipment or personnel in the vicinity. Therefore, this embodiment is designed for use with laser sources with a contact-type laser interlock deactivation system. This type of interlock deactivation system could be one of two or more types of systems in use, i.e. either mechanical contact and interlock deactivation or electrical contact which thereby completes a circuit which controls the interlock. In the embodiment of FIGS. 15-18, either type of laser interlock deactivation system can be used, the particular system depending upon the laser source electronics and application.

Figure 18:
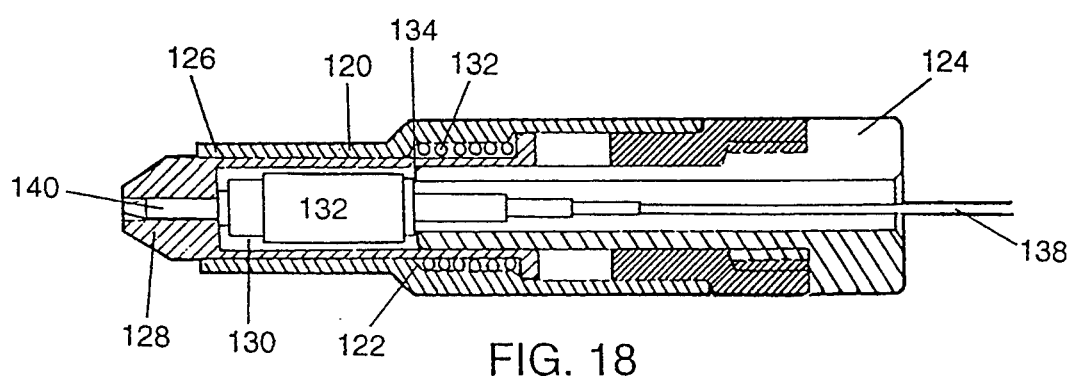
FIG. 18 is a side cross section view of an embodiment of the apparatus of the present invention with a fiber optic laser delivery device installed therein.

A generally conical shaped central member 128 is formed so as to make an electrical or mechanical contact with the laser source output port, only when the fiber optic laser delivery device is present. The inside annular region 130 of the proximal end of the connector plug portion is shaped to receive the fiber connector 132 of the fiber device. This conical shaped central member forms a physical matching connection between the laser source and the fiber optic laser delivery device by positioning the proximal end of the fiber optic laser delivery device accurately and precisely adjacent to the output port of the laser source, thereby allowing laser energy to be communicated directly and efficiently from the laser source into the proximal end of the fiber optic laser delivery device. However, not until the distal end 134 of the fiber securing portion can be engaged by threads 136 or some other attachment means of the fiber securing portion, will the retractable tip be extended. This engagement can be accomplished by providing matching, keyed portions or other detachable connecting means, shown here as a set of threads which can be couples with a set of matching threads in the distal end of the connector plug portion. Therefore, as best shown in FIG. 18, the fiber optic laser delivery device is held securely in place by being inserted into the connector plug portion of the reusable connector and having the fiber securing portion screwed onto the end. A slot 82 is provided in the fiber securing portion so as to allow the portion to be slipped over the fiber optic portion of the laser delivery device and assembled efficiently and conveniently. Thus, the fiber optic portion 84 of the fiber optic laser delivery system is shown to extend from the distal end of the fiber securing portion of the reusable connector adapter.

A spring member 132 maintains the retracted tip inside the end of the connector plug portion when a fiber device is not inserted. As the fiber connector of the fiber optic laser delivery device is inserted into the distal end of the connector plug portion and the fiber securing portion is threaded onto the end of the connector, the spring member is compressed and the retracted tip extends from the proximal end of the device so as to provide a contact for the interlock deactivation system.

As an additional safety feature of the invention, an optical barrier is installed in the conical shaped central member. This optical barrier is held in a normally closed position by a spring. Thus, in the event the reusable connector adapter is connected to a laser source and the laser source interlock system is deactivated and laser transmission is initiated without first inserting a fiber optic laser delivery device, then there will be no opportunity for the laser source to be released into the surrounding operating room or other environment. This is very important in operation. As is well known, a stray laser beam in a medical operating room or in any other application would have the potential to cause serious damage to surgeons, technicians, patients, observers, or any equipment in the vicinity.

It is important to note that the present invention includes the embodiment wherein a bare fiber is inserted into the reusable connector adapter. In this application, where a fiber has a bare end or other simple fitting, but is to be used to direct a laser beam, the bare fiber or other simple fitting could be inserted into the adapter. This embodiment would be slightly different than those previously described. With regard to the design of the connector plug portion, the internal annular opening for receiving the fiber connector would be somewhat smaller. Furthermore, the fiber securing portion will be designed specifically for maintaining bare fibers in close proximity with the adapter so that the entire assembly can be mounted onto a laser source output port.

It will be understood that the embodiments shown and described herein are typical and representative of but a few of the embodiments of the present invention designed specifically for compatibility and adaptability among and between the plethora of available equipment. Therefore, modifications and slight improvements or adaptations for other configurations of laser source as well as fiber optic laser delivery device may be obvious to those knowledgeable, trained or skilled in the art. A variety of methods are available for securing connectors to fibers, interfacing the fiber optic laser delivery device with the laser output port, securing the fiber/connector assembly to the adaptor, etc. and all of these existing or future methods and designs will be incorporated herein.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A reusable connector adapter for coupling a laser source to a fiber optic laser delivery device, the laser source having an output port for transmitting laser energy, the laser source having a laser interlock for preventing the undesired transmission of laser energy unless and until such time as said interlock is deactivated, said laser interlock requiring an electrical signature generated by an electrical signature generating circuit for deactivation of said laser interlock, the fiber optic laser delivery device having a laser receiving end with a fiber connector at said laser receiving end, said fiber optic laser delivery device further having a fiber optic waveguide, said reusable connector adapter comprising:

a connector plug portion, said connector plug portion having a proximal end precisely shaped so as to couple efficiently with said laser source, said proximal end of said connector plug portion having a laser source attachment means such that said connector plug portion can be securely maintained adjacent to said output port of said laser source in an operative position, said connector plug portion further having a distal end, said connector plug portion further having a central hollow body portion intermediate said proximal end and said distal end for receiving and containing said fiber connector within said central hollow body portion in efficient optical communication with said laser source, said connector plug portion further having a laser interlock deactivation means, said laser interlock deactivation means comprising an electrical signature generating circuit;

a fiber optic laser delivery device securing portion for removably maintaining and securing said fiber optic laser delivery device within said central hollow body portion of said connector plug portion; and an optical barrier for preventing said laser energy from being transmitted, said optical barrier comprised of an optically opaque material, said optical barrier preventing said laser energy from being transmitted unless a fiber optic laser delivery device is properly installed within said reusable connector adapter.

2. The invention of claim 1 wherein said optical barrier is mounted within said central hollow body portion of said connector plug portion such that upon insertion of the fiber optic laser delivery device into the reusable connector adapter, the optical barrier is removed from the path of transmission of laser energy.

3. The invention of claim 1 wherein said optical barrier is adjacent said proximal end of said connector plug portion.

4. The invention of claim 1 wherein said optical barrier is adjacent said fiber optic laser delivery device securing portion of said reusable connector adapter.

5. The invention of claim 1 wherein said optical barrier is pivotally mounted on a spring member.

6. The invention of claim 1 wherein said optical barrier is mounted within said central hollow body portion of said connector plug portion adjacent to said distal end of said connector plug portion.

7. The invention of claim 1 wherein said laser interlock system requires a mechanical or electrical contact between said proximal end of said connector plug portion and said output port of said laser source for deactivation, and said laser interlock deactivation means comprises a contacting element.

8. The invention of claim 7 wherein said contacting element is retractable.

9. The invention of claim 8 wherein said retractable contacting element is in a retracted position in the absence of said fiber optic laser delivery device and in an extended position when said fiber connector of said fiber optic laser delivery device is received within said connector plug portion, whereby when said retractable element is extended, said contacting element is in electrical, mechanical or optical contact with said output port of said laser source.

10. The invention of claim 1 wherein said fiber optic laser delivery device securing portion comprises an engagement means for coupling said fiber optic laser delivery device securing portion to said connector plug portion thereby maintaining said fiber optic laser delivery device within said central hollow body portion.

11. The invention of claim 10 wherein said engagement means comprises a biasing element for maintaining said fiber optic laser delivery device within said central hollow body portion biased between said connector plug portion and said fiber optic laser delivery device securing portion.

12. A reusable connector adapter for coupling a laser source to a fiber optic laser delivery device, the laser source having an output port for transmitting laser energy, the laser source having a laser interlock for preventing the undesired transmission of laser energy unless and until such time as the interlock is deactivated, the laser interlock comprising an optical switch for deactivation of the laser interlock, the fiber optic laser delivery device having a laser receiving end with a fiber connector at the laser receiving end, the fiber optic laser delivery device further having a fiber optic waveguide, the reusable connector adapter comprising:

a connector plug portion, the connector plug portion having a proximal end precisely shaped so as to couple efficiently with the laser source, the proximal end of the connector plug portion having a laser source attachment means such that the connector plug portion can be securely maintained adjacent to the output port of the laser source in an operative position, the connector plug portion further having a distal end, the connector plug portion further having a central hollow body portion intermediate the proximal end and the distal end for receiving and containing the fiber connector within the central hollow body portion in efficient optical communication with the laser source, the connector plug portion further having a laser interlock deactivation means, the laser interlock deactivation means supplying an optical signal such that the laser source interlock is deactivated;

a fiber optic laser delivery device securing portion for removably maintaining and securing the fiber optic laser delivery device within the central hollow body portion of the connector plug portion; and an optical barrier for preventing the laser energy from being transmitted, the optical barrier comprised of an optically opaque material, the optical barrier preventing the laser energy from being transmitted unless a fiber optic laser delivery device is properly installed within the reusable connector adapter.

13. The invention of claim 12 wherein the optical barrier is mounted within the central hollow body portion of the connector plug portion such that upon insertion of the fiber optic laser delivery device into the reusable connector adapter, the optical barrier is removed from the path of transmission of laser energy.

14. The invention of claim 12 wherein the optical barrier is adjacent the proximal end of the connector plug portion.

15. The invention of claim 12 wherein the optical barrier is adjacent the fiber optic laser delivery device securing portion of the reusable connector adapter.

16. The invention of claim 12 wherein the optical barrier is pivotally mounted on a spring member.

17. The invention of claim 12 wherein the optical barrier is mounted within the central hollow body portion of the connector plug portion adjacent to the distal end of the connector plug portion.

18. The invention of claim 12 wherein the laser interlock system requires a mechanical or electrical contact between the proximal end of the connector plug portion and the output port of the laser source for deactivation, and the laser interlock deactivation means comprises a contacting element.

19. The invention of claim 18 wherein the contacting element is retractable.

20. The invention of claim 19 wherein the retractable contacting element is in a retracted position in the absence of the fiber optic laser delivery device and in an extended position when the fiber connector of the fiber optic laser delivery device is received within the connector plug portion, whereby when the retractable element is extended, the contacting element is in electrical, mechanical or optical contact with the output port of the laser source.

21. The invention of claim 12 wherein the fiber optic laser delivery device securing portion comprises an engagement means for coupling the fiber optic laser delivery device securing portion to the connector plug portion thereby maintaining the fiber optic laser delivery device within the central hollow body portion.

22. The invention of claim 21 wherein the engagement means comprises a biasing element for maintaining the fiber optic laser delivery device within the central hollow body portion biased between the connector plug portion and the fiber optic laser delivery device securing portion.

23. A reusable optical fiber connector adapter for coupling a laser source and a fiber optic laser delivery device, the laser source having an output port for transmitting laser energy and having a laser interlock for preventing the undesired transmission of laser energy unless and until such time as the interlock is deactivated, the laser interlock comprising control circuitry to block the production of a laser beam by the laser source and further comprising a mechanical switch for deactivation of the laser interlock, the fiber optic laser delivery device having a fiber optic waveguide and having a laser receiving end with a fiber, connector at the laser receiving end, the reusable connector adapter comprising:

a connector plug portion, the connector plug portion having a proximal end with a predetermined shape to optically couple with the output port of the laser source, the proximal end of the connector plug portion having a laser source output port attachment to securely maintain the connector plug portion in precise alignment adjacent to the output port of the laser source in an operative position, the connector plug portion further having a distal end, the connector plug portion further having a central hollow body portion intermediate the proximal end and the distal end for receiving and containing the fiber connector within the central hollow body portion in efficient optical communication with the laser source, the connector plug portion further having a laser interlock deactivator, whereby the laser interlock deactivator acts upon the interlock mechanical switch thereby causing the control circuitry to deactivate the interlock and permit the laser source to produce laser energy when the adapter connector is coupled to the laser source;

a fiber optic laser delivery device securing portion for removably maintaining and securing the fiber optic laser delivery device within the central hollow body portion of the connector plug portion; and an optical barrier for preventing the laser energy from being transmitted, the optical barrier comprised of an optically opaque material, the optical barrier optically preventing the laser energy from being transmitted unless a fiber optic laser delivery device is properly installed within the reusable connector adapter.

24. The invention of claim 23 wherein the optical barrier is mounted within the central hollow body portion of the connector plug portion such that upon insertion of the fiber optic laser delivery device into the reusable connector adapter, the optical barrier is removed from the path of transmission of laser energy.

25. The invention of claim 23 wherein the optical barrier is adjacent the proximal end of the connector plug portion.

26. The invention of claim 23 wherein the optical barrier is adjacent the fiber optic laser delivery device securing portion of the reusable connector adapter.

27. The invention of claim 23 wherein the optical barrier is pivotally mounted on a spring member.

28. The invention of claim 23 wherein the optical barrier is mounted within the central hollow body portion of the connector plug portion adjacent to the distal end of the connector plug portion.

29. The invention of claim 23 wherein the laser interlock system requires a mechanical, electrical or optical contact between the proximal end of the connector plug portion and the output port of the laser source for deactivation, and the laser interlock deactivator comprises a contacting element.

30. The invention of claim 29 wherein the contacting element is retractable.

31. The invention of claim 30 wherein the retractable contacting element is in a retracted position in the absence of the fiber optic laser delivery device and in an extended position when the connector of the fiber optic laser delivery device is received within the connector plug portion, whereby when the retractable element is extended, the contacting element is in mechanical, electrical or optical contact with the output port of the laser source.

32. The invention of claim 23 wherein the fiber optic laser delivery device securing portion comprises an engagement means for coupling the fiber optic laser delivery device securing portion to the connector plug portion thereby maintaining the fiber optic laser delivery device within the central hollow body portion.

33. The invention of claim 32 wherein the engagement means comprises a biasing element for maintaining the fiber optic laser delivery device within the central hollow body portion biased between the connector plug portion and the fiber optic laser delivery device securing portion.

* * * * *